(12) United States Patent
Salick et al.

(10) Patent No.: US 8,426,559 B2
(45) Date of Patent: Apr. 23, 2013

(54) **INJECTABLE β-HAIRPIN PEPTIDE HYDROGEL THAT KILLS METHICILLIN-RESISTANT *STAPHYLOCOCCUS AUREUS***

(75) Inventors: Daphne A. Salick, Lawrenceville, NJ (US); Darrin J. Pochan, Landenburg, PA (US); Joel P. Schneider, Middletown, MD (US)

(73) Assignee: University of Delaware, Newark, DE (US)

( * ) Notice: Subject to any disclaimer, the term of this patent is extended or adjusted under 35 U.S.C. 154(b) by 202 days.

(21) Appl. No.: 12/730,656

(22) Filed: Mar. 24, 2010

(65) Prior Publication Data

US 2011/0171304 A1 Jul. 14, 2011

Related U.S. Application Data

(60) Provisional application No. 61/162,810, filed on Mar. 24, 2009.

(51) Int. Cl.
*C07K 7/00* (2006.01)
(52) U.S. Cl.
USPC ............................................. 530/326; 514/2.3
(58) Field of Classification Search .................. 530/326; 514/2.3
See application file for complete search history.

(56) References Cited

U.S. PATENT DOCUMENTS

| | | | |
|---|---|---|---|
| 2006/0025524 A1 | 2/2006 | Schneider et al. |
| 2007/0128175 A1 | 6/2007 | Ozbas et al. |
| 2009/0238788 A1 | 9/2009 | Butterick et al. |
| 2010/0034881 A1 | 2/2010 | Schneider et al. |

OTHER PUBLICATIONS

Salick, Daphne A., et al.; "Inherent Antibacterial Activity of a Peptide-Based β-Hairpin Hydrogel"; J. Am. Chem. Soc.; 2007; vol. 129; pp. 14793-14799.
Schneider, Joel P., et al.; "Responsive Hydrogels from the Intramolecular Folding and Self-Assembly of a Designed Peptide"; J. Am. Chem. Soc.; 2002; vol. 124; pp. 15030-15037.
Pochan, Darrin J., et al.; "Thermally Reversible Hydrogels via Intramolecular Folding and Consequent Self-Assembly of a *de Novo* Designed Peptide"; J. Am. Chem. Soc.; 2003; vol. 125; pp. 11802-11803.
Haines-Butterick, L.A. et al. In Vitro Assessment of the Proinflammatory Potential of Beta-Hairpin Peptide Hydrogels. Biomaterials, 2008, vol. 29, pp. 4164-4169.
Kretsinger, J.K. et al. Cytocompatibility of Self-Assembled Beta-Hairpin Peptide Hydrogel Surfaces. Biomaterials, 2005, vol. 26, pp. 5177-5186.
Hule, R.A. et al. Correlations Between Structure, Material Properties and Bioproperties in Self-Assembled Beta-Hairpin Peptide Hydrogels. Faraday discuss., 2008, vol. 139, pp. 251-264.
International Search Report dated Mar. 18, 2011, application No. PCT/US2010/028435.

*Primary Examiner* — David Lukton
(74) *Attorney, Agent, or Firm* — RatnerPrestia

(57) ABSTRACT

A peptide comprising the sequence VKVKVRVKV$^D$PPT-KVKVRVKV-NH$_2$ forms a hydrogel which has the ability to shear-thin and recover. The hydrogel, both before and after shear-thinning, is capable of killing bacteria, including methicillin-resistant *Staphylococcus aureus* (MRSA).

7 Claims, 11 Drawing Sheets

Scale bar = 200 μm

INJECTABLE β-HAIRPIN PEPTIDE HYDROGEL THAT KILLS METHICILLIN-RESISTANT *STAPHYLOCOCCUS AUREUS*

CROSS REFERENCE TO RELATED APPLICATIONS

This application claims priority of U.S. provisional patent application No. 61/162,810, filed Mar. 24, 2009, the entirety of which is incorporated herein by reference.

STATEMENT REGARDING FEDERALLY SPONSORED RESEARCH

Research leading to the disclosed invention was funded with funds from the National Institute of Dental and Craniofacial Research under Contract No. R01 DE01638601. Accordingly, the United States government has certain rights in the invention described herein.

BACKGROUND OF THE INVENTION

In general, infection at a wound site prolongs healing, and with respect to medical implants, infection at the implant-tissue interface can result in implant failure. Thus, the ability to control and prevent infections is of critical importance in the medical field. One common infectious bacterium, *Staphylococcus aureus*, has traditionally been treated with standard antibiotics. However, drug resistant bacterial strains have evolved. Methicillin-resistant *Staphylococcus aureus* (MRSA) infections have become common and account for about 55% of all nosocomial infections acquired in intensive care units in the United States. This bacterium is also frequently found in isolates of medical implant-related infections. MRSA is resistant to conventional β-lactam antibiotics, and thus, MRSA infections are normally treated with a combination of drugs, such as quinupristin and dalfopristin, that inhibit the early and late stages of protein synthesis, respectively. However, there is concern that MRSA may eventually evolve resistance to these therapies as well. Thus, new antibiotics capable of killing MRSA are urgently sought.

SUMMARY OF THE INVENTION

The invention provides a peptide comprising the sequence VKVKVRVKV$^D$PPTKVKVRVKV-NH$_2$, and hydrogels comprising a peptide having that sequence. The invention further provides a method of killing bacteria that includes a step of contacting the bacteria with a hydrogel comprising a peptide that comprises the sequence VKVKVRVKV$^D$PPTKVKVRVKV-NH$_2$.

BRIEF DESCRIPTION OF THE DRAWINGS

FIG. 2A shows the results for a surface infected with MRSA. FIG. 2B shows the results for a surface infected with MSSA (methicillin-susceptible *Staphylococcus aureus*).

DETAILED DESCRIPTION OF THE INVENTION

Figure 1:
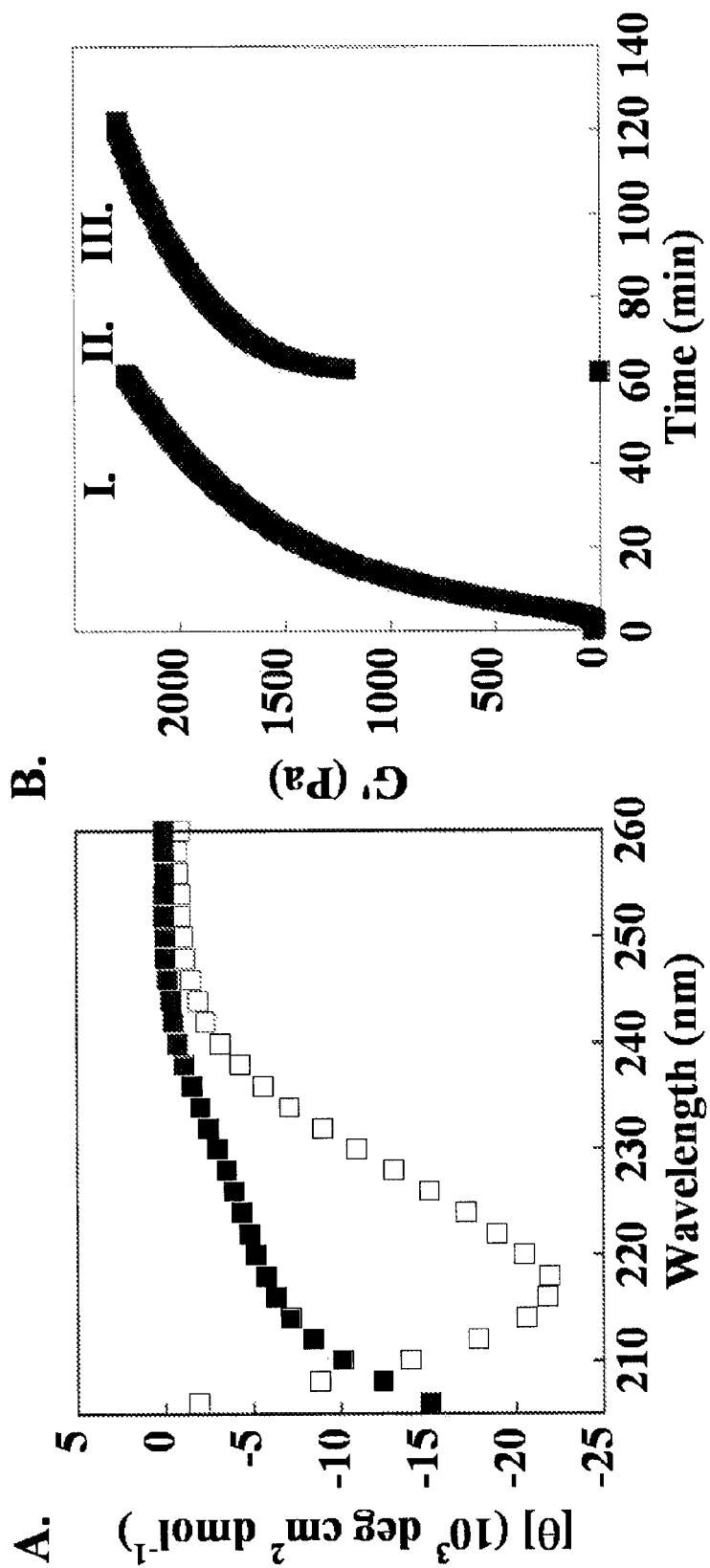
FIG. 1A shows circular dichroism (CD) wavelength spectra of MARG1 in water before (■) and after (□) the addition of DMEM cell culture media.
FIG. 1B shows an oscillatory shear rheological experiment monitoring bulk hydrogel formation and shear-thinning/recovery.

The inventors have found a specific peptide sequence that is capable of forming a hydrogel that effectively kills MRSA on contact. This sequence, identified herein as MARG1, is shown below.

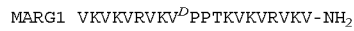

MARG1 VKVKVRVKV$^D$PPTKVKVRVKV-NH$_2$

MARG1 forms a hydrogel that shear-thins and rapidly re-forms upon cessation of shearing, so that the peptide hydrogel can be applied by injection via a syringe or other similar device to a contaminated surface where it kills MRSA on contact. The hydrogel can also be used as a coating to inhibit MRSA infection.

MARG1 is related to a previously known peptide, MAX1 (shown below), but the inventors have found the antibiotic properties of MARG1 are significantly stronger than those of MAX1, particularly against MRSA.

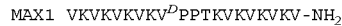

MAX1 VKVKVKVKV$^D$PPTKVKVKVKV-NH$_2$

While it was previously known that MAX1 showed antibacterial behavior towards a range of drug-susceptible gram positive and gram negative bacteria, there was no evidence that it would be effective against MRSA. It is well known that MRSA is resistant to many antibiotics that are effective against non-resistant *Staphylococcus aureus*, and indeed the inventors have found that MAX1 has only marginal effectiveness against MRSA. In contrast, MARG1 is very effective.

MARG1 hydrogels according to the invention are well hydrated solid materials and have a stiffness greater than 40 Pa, as measured by the storage modulus G' at a strain of 0.2%. Above approximately 40 Pa the material is a self-supporting solid gel material. The stiffness can reach greater than 10,000

Pa at higher peptide concentration. The hydrogels typically contain at least 0.5 wt % peptide in an aqueous medium.

Addition of DMEM cell culture media (Dulbecco's Modified Eagle's Medium) to a solution of MARG1 or MAX1 results in hydrogelation, apparently due to folding and self-assembly of the peptides. It is thought that the peptides adopt an amphiphilic β-hairpin that is prone to self-assembly. Once folded, the hairpin assembles into a network of β-sheet rich fibrils that produces a mechanically rigid hydrogel. The resultant gels display shear-thinning/recovery properties, allowing them to be delivered by a syringe.

When MARG1 is dissolved in water, it remains unfolded and soluble due to the charge repulsion between positively charged side chains. However, MARG1 folds when an equal volume of DMEM cell culture media, which contains ~160 mM mono- and divalent salts, is added at temperatures at/or above room temperature. The pH of the mixture at this point is approximately 7.4. The salt is believed to screen the side chain-derived charge and allows the peptide to fold. MARG1 incorporates an amphiphilic β-hairpin containing two β-strands connected by a four residue (-V$^D$PPT-) type II' β-turn. The strand regions of the hairpin contain alternating sequences of valine and charged residues (Lys/Arg) such that in the folded state, one face (the valine-rich face) of the hairpin is hydrophobic and the opposing face (the lysine/arginine face) is lined with positively charged side chains and is hydrophilic. MARG1 forms a hydrogel at a pH of about 7 or higher. Alternatively, a hydrogel can also be formed by including a high enough content of NaCl or other salts, usually in a range from 100 mM-300 mM. Increasing pH and increasing ionic strength both encourage hydrogel formation, and the two effects are at least roughly additive. Thus, the lower the pH, the higher the salt concentration necessary for hydrogel formation. In the presence of sufficient salt(s), MARG1 can form a hydrogel at a pH at least as low as about 6.

MARG1 self-assembly may involve formation of a network of intermolecular hydrogen bonds that defines the long axis of a given fibril. This self-assembly may result in a structure having a hydrophobic face shielded from water, thus forming a bilayer that defines the thickness of the fibril. Whatever the exact mechanism, gels can be formed directly in, and delivered from, a syringe.

The MARG1 sequence differs from that of MAX1 in that it contains Arg residues, rather than Lys residues, at positions 6 and 17. Without wishing to be bound by any particular theory or explanation, the inventors consider that these differences may allow MARG1 to engage in specific interactions with the outermost components of the MRSA bacteria cell in a way that is different from, or at least more effective than, that found for the similar MAX1 peptide. Whatever the reason, MARG1 is substantially more effective than MAX1 for killing MRSA, as will be seen later herein.

MARG1 Hydrogel Formation and Physical Properties

The initial formation of the MARG1 hydrogel can be followed spectroscopically. FIG. 1A shows circular dichroism (CD) wavelength spectra of MARG1 in water before (■) and after (□) the addition of DMEM cell culture media. Dissolved in water, MARG1 adopts a random coil conformation, displaying a spectrum consistent with this unfolded state. However, when an equal volume of DMEM cell culture media is added directly to the aqueous peptide solution, MARG1 folds and assembles into a β-sheet rich hydrogel as indicated by the strong negative ellipticity at 216 nm.

The resultant hydrogel is mechanically rigid and displays shear-thinning/recovery behavior. MARG1 gels shear-thin when a shear stress is applied, such as when delivered by syringe. This converts the gel to a lower viscosity, flowable fluid. The shear stress is relieved when the fluid exits the syringe and the gel quickly self-heals, recovering its original mechanical rigidity. This shear-thinning/recovery mechanism allows the MARG1 gel to be easily delivered by syringe to effectively match the shape of the target site.

FIG. 1B shows an oscillatory shear rheological experiment monitoring bulk hydrogel formation and shear-thinning/recovery. The gelation of an aqueous solution of MARG1 was triggered on the rheometer by the equal-volume addition of DMEM, resulting in a gel containing 2 wt % MARG1. The mechanical rigidity of the forming hydrogel was assessed by measuring the storage modulus (G', the elastic response of the material to applied strain) as a function of time at 0.2% strain. Regime I shows the formation of the hydrogel after initiating folding and self-assembly at 37° C. A storage modulus of 500 Pa was realized after several minutes showing that a moderately rigid gel quickly forms that rigidifies over time (2,200 Pa gel at 60 minutes). In Regime II, 1000% strain was applied to the gel and the gel shear-thinned, resulting in a low viscosity solution. After the cessation of high strain (regime III), the hydrogel quickly self-healed, recovering about 50% of it original rigidity in seconds. At that point in time, the gel had become self-supporting. Gels sheared in this manner fully recover over time (not shown here). Similarly, when bulk MARG1 gels are delivered by syringe, they instantaneously recover after exiting the syringe and remain localized at the site of application.

MARG1 Hydrogel Antibacterial Properties

The antibacterial activity of MARG1 hydrogels was assessed via two distinct assays. In the first assay, bacteria were introduced to the surface of tissue culture treated polystyrene (TCTP) coated with a ~1-2 mm layer of the gel and its ability to inhibit bacterial proliferation was assessed. This assay measures the ability of MARG1 gels to thwart new infection at a particular site. Here, gels were formed directly on the polystyrene surface without the aid of shear-thin delivery. In the second assay, MARG1 gels were shear-thin delivered via syringe to agar surfaces infected with bacteria, and the ability of the gel to kill bacteria on contact was measured. This assay simulates the introduction of the MARG1 gel via syringe to a bacterial contaminated surface, such as a wound.

Figure 2:
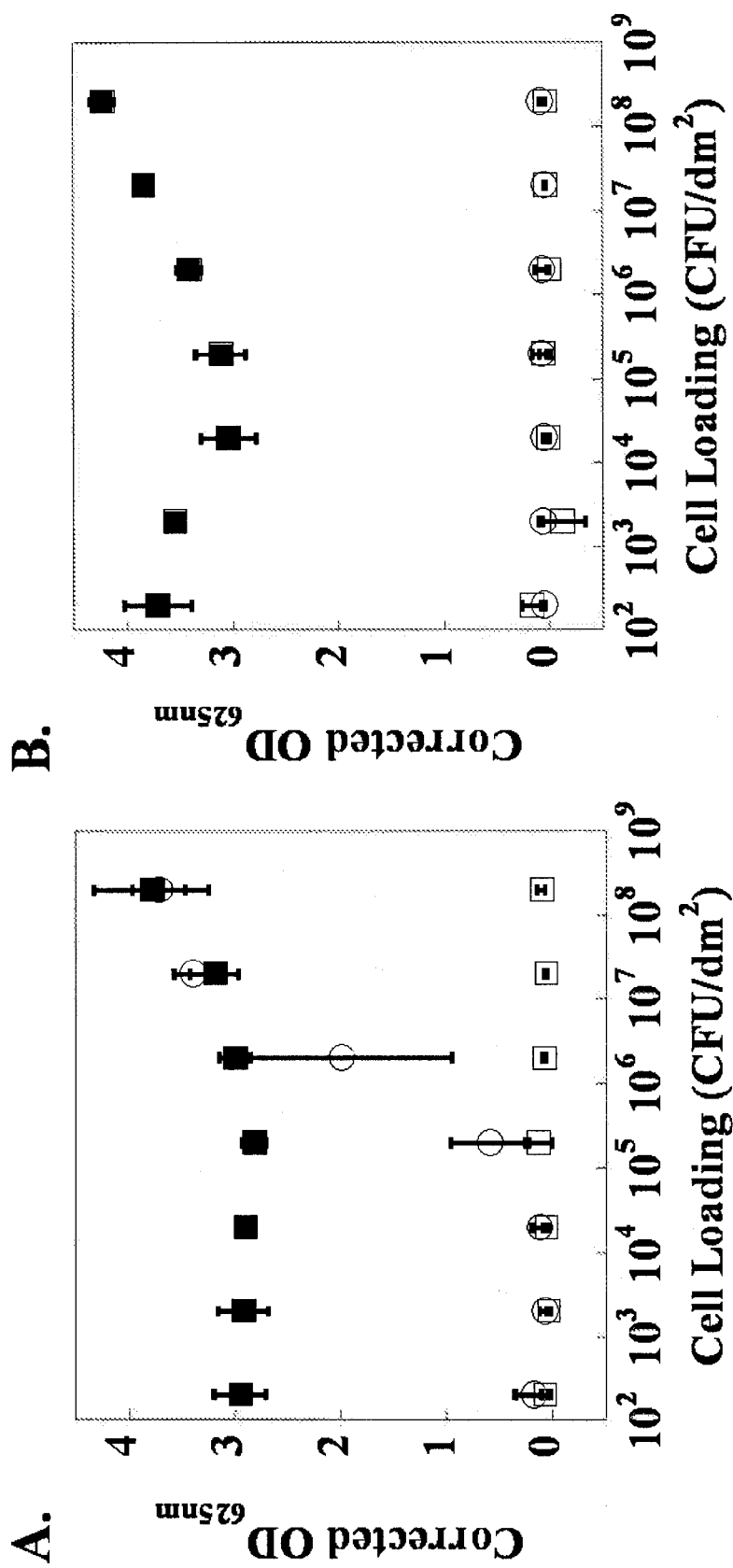
FIG. 2 shows the results of assays where MARG1 (□) and MAX1 (○) hydrogel surfaces were challenged with increasing numbers of bacteria as compared to a TCTP control (■) surface.

FIG. 2 shows results obtained from the first type of assay, with OD (optical density) being measured 24 hours post challenge for a TCTP control surface (■), a 2 wt % MARG1 (□) hydrogel surface and a 2 wt % MAX1 (○) surface. FIG. 2A shows results of an assay in which an increasing number of colony-forming units (CFU's) of MRSA were introduced to uncoated and hydrogel coated TCTP surfaces. The gels were incubated for 24 hr at 37° C., and bacterial proliferation was quantitated by light scattering as described in Salick, D. A.; Kretsinger, J. K.; Pochan, D. J.; Schneider, J. P. *J. Am. Chem. Sci.* 2007, 129, 14793. In addition, MRSA was also introduced to TCTP surfaces coated with the control MAX1 gel to assess the importance of the arginine residues to the design of MARG1. The bacterial cell loading densities used in this assay are exceedingly high and provide a stringent assessment of antibacterial activity of the gel surfaces. FIG. 2A shows that when $2\times10^2$ to $2\times10^8$ CFU/dm$^2$ of MRSA were introduced to the uncoated TCTP surface, MRSA was capable of uninhibited proliferation. However, the MARG1 coated surface was capable of complete inhibition of MRSA proliferation even when the coated surface was challenged with $2\times10^8$ CFU/dm$^2$ of the bacteria. Interestingly, the same assay performed with the control MAX1 coated surface shows that this hydrogel is capable of inhibiting MRSA at lower CFUs, but loses its antibacterial capacity at higher cell loading densities. For example at $2 \times 10^8$ CFU/dm$^2$ of MRSA, MAX1 coated surfaces were overwhelmed and allowed uninhibited MRSA proliferation, whereas MARG1 coated surfaces were still completely active against MRSA. The reason that this difference in activity resulted from merely replacing two specific lysine residues with arginines is not clear, but the significant effect of this change is quite apparent.

FIG. 2B shows data from similar assays that were performed using methicillin-susceptible *Staphylococcus aureus* (MSSA). These data show that both MARG1 and the control MAX1 surfaces can inhibit bacterial proliferation as compared to the uncoated surface, at all bacterial cell loading densities. It can be concluded that the MAX1 hydrogels provided significant activity against strains that are not methicillin-resistant, but MARG1 provided significantly enhanced action against the methicillin-resistant strain compared with that provided by MAX1.

Figure 3:
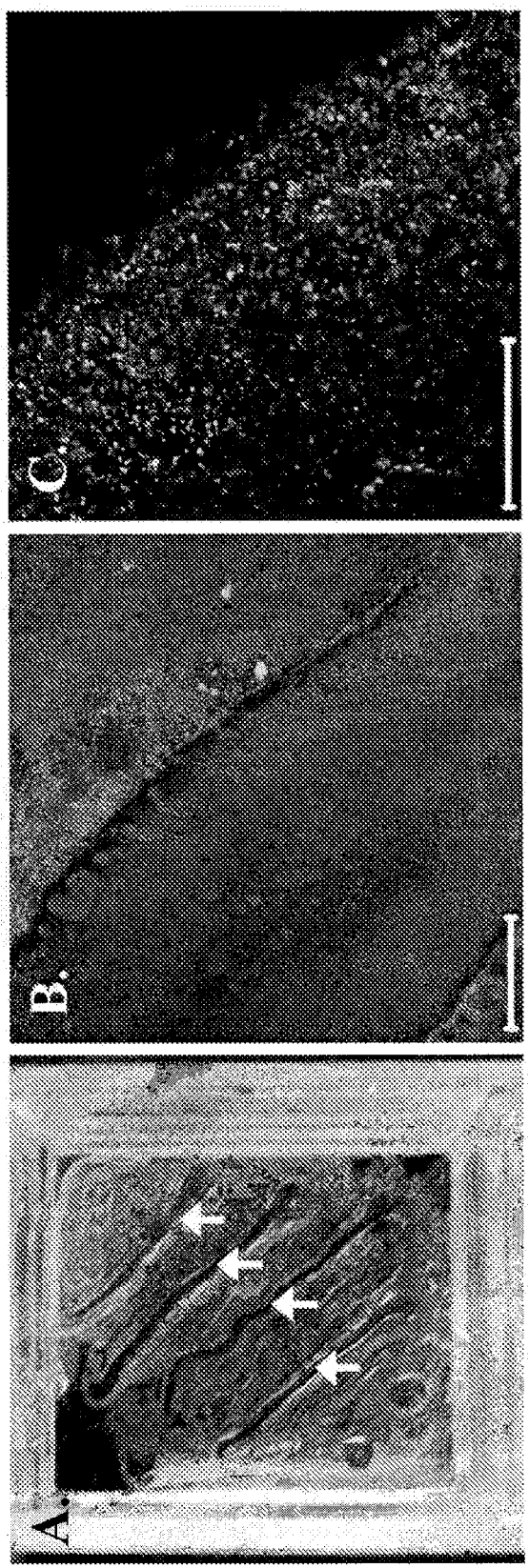
FIG. 3A shows a plate where hydrogel was delivered onto a bacteria-infected surface.
FIGS. 3B,C are black and white renderings of laser scanning confocal microscopy (LSCM) images of live/dead viability assays, taken at different magnifications, showing the perimeter of hydrogel that had been sheared onto a bacteria-loaded agar plate.

FIGS. 3A-C are micrographs illustrating the results of the second type of assay, where 2 wt % of MARG1 hydrogel was shear-thin delivered via syringe to a lawn of MRSA that had been cultured on a nutrient-rich agar surface. The hydrogel was delivered onto the infected surface as individual streaks from the top left to the bottom right of the plate (FIG. 3A; see arrows) making diagonal lines as shown. In these assays, samples were allowed to incubate for 24 hours, providing sufficient time for bacterial growth where nutrients are provided from the underlying agar. Visual assessment of the underlying agar shows the absence of bacterial growth beneath the delivered hydrogel, where the agar has remained clear. However, bacterial growth is seen on the outlying agar that was not exposed to hydrogel, where the agar appears opaque.

To assess the viability of bacteria that had come into contact with the hydrogel, a live/dead viability assay employing laser scanning confocal microscopy was performed. In this assay, dyes were added after the 24 hour incubation period. Live cells fluoresce green and dead cells fluoresce red, as described in Salick, D. A.; Kretsinger, J. K.; Pochan, D. J.; Schneider, J. P. *J. Am. Chem. Sci.* 2007, 129, 14793. FIGS. 3B,C are black and white renderings of laser scanning confocal microscopy (LSCM) images of live/dead viability assays showing the perimeter of the hydrogel that had been sheared onto the bacteria-loaded agar. Green (live cell) areas in the original micrographs in FIGS. 3B,C show up as light areas and red (dead cell) areas show up as dark areas. In FIG. 3B, the broad dark band which appears diagonally across the image from the top left to the bottom right shows the location of the hydrogel streak, where there are dead cells. The lower left corner and the upper right section of FIG. 3B, where there is no hydrogel, are mostly light-shaded, indicating live cells. Thus, bacterial cells that came into contact with the hydrogel were effectively killed. FIG. 3C is a magnified image of the agar-hydrogel border, where individual live cocci are evident as light-shaded specks and the dark region in the upper right portion of the micrograph includes dead cells, where the bacteria that have come into contact with the hydrogel are dead.

Figure 4:
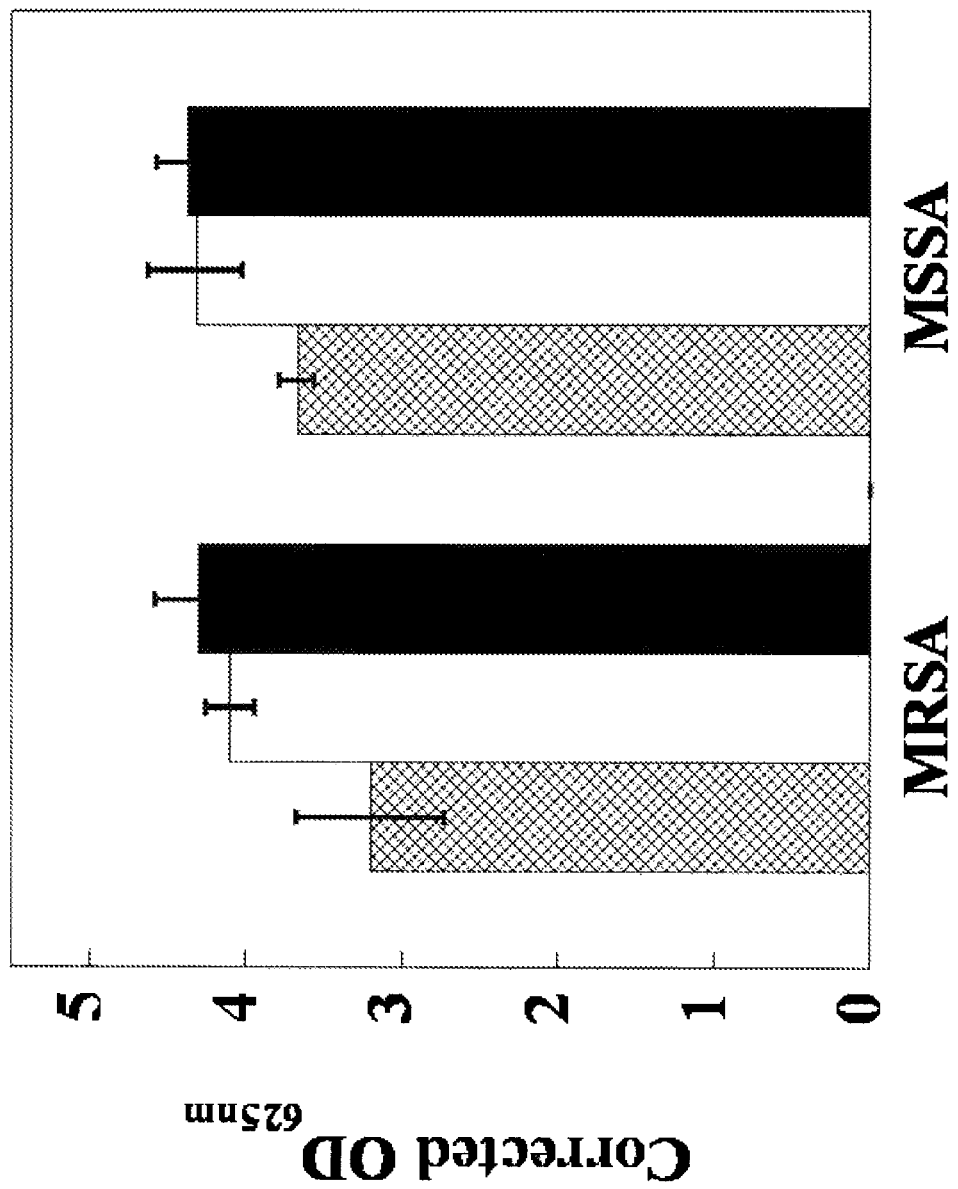
FIG. 4 shows proliferation of MRSA and MSSA on a TCTP control surface in the absence of peptide, in the presence of 100 μM soluble (folded but not gelled) MARG1, and in the presence of 100 μM soluble (folded but not gelled) MAX1.

The live/dead assays shown in FIGS. 3A-C suggest that MRSA must come into contact with the hydrogel surface in order to be killed. Further experiments indicated that peptide diffusing from the gel is not the active agent. When both MRSA and MSSA were subjected to 100 µM aqueous solutions (i.e., not hydrogels) of MARG1, bacterial proliferation was minimally affected (See FIG. 4). This concentration of peptide is significantly higher than the measurable amount of free peptide which diffuses into the tryptic soy broth in a typical bacterial assay. FIG. 4 shows proliferation of $2 \times 10^6$ CFU/dm$^2$ MRSA (left) and MSSA (right) on a TCTP control surface in the absence of peptide (checkered bars), in the presence of 100 µM solutions of MARG1 (white bars), and in the presence of 100 µM solutions of MAX1 (black bars). The data in FIG. 4 has an N value of 3.

Figure 5:
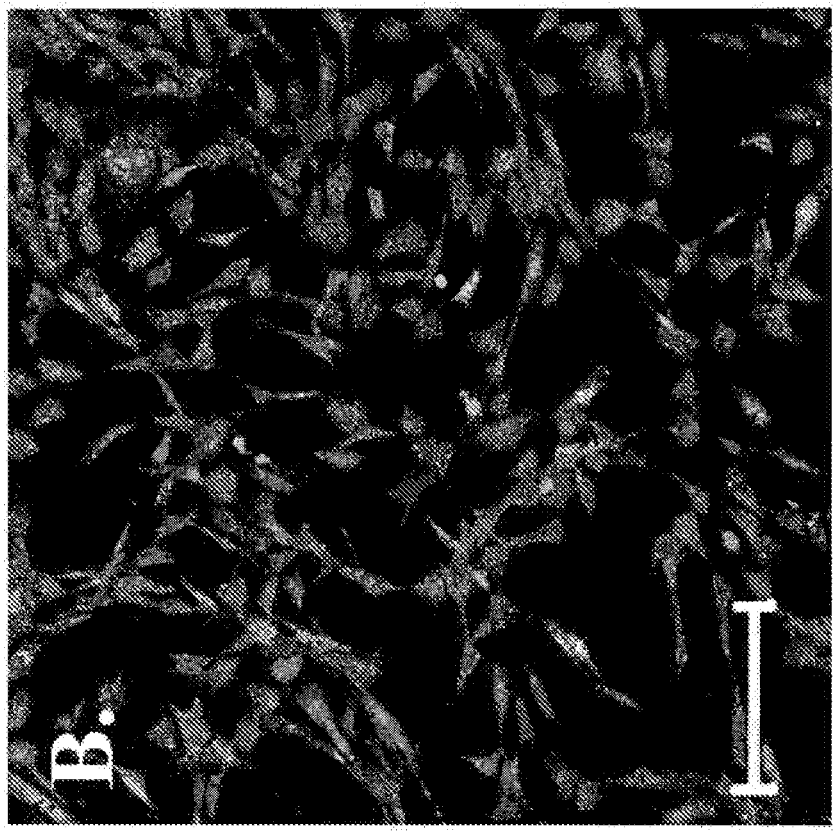
FIGS. 5A,B are micrographs indicating non-cytotoxicity of MARG1 towards mammalian cells.
Figure 5:
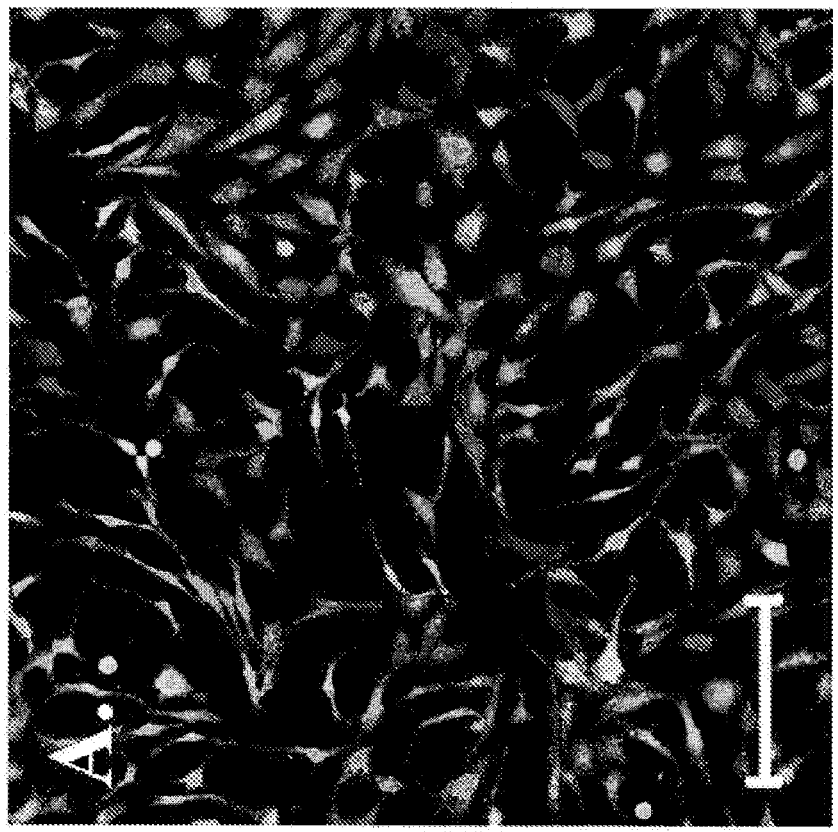

FIGS. 5A,B show micrographs indicating that although the MARG1 gel is active against *Staphylococcus aureus*, and particularly against MRSA, it is non-cytotoxic towards mammalian cells. The confocal images show live/dead viability assays performed using murine C3H10t1/2 mesenchymal stem cells that had been cultured for 24 h on (A) a 2 wt % MARG1 hydrogel surface and on (B) a TCTP control surface. This cell line was chosen because these cells are sensitive to their environment and thus good indicators of a material's cytotoxic properties.

The images in FIGS. 5A,B are rendered in black and white, where the light areas represent cells that fluoresce green (live cells) and dark areas represent cells that fluoresce red (dead cells). Dead cells were not evident in the original color micrograph for FIG. 5A, and only one small, barely visible feature in FIG. 5B (TCTP control surface) showed the presence of a dead cell. There was no significant difference in the viability of cells cultured on the surface of MARG1 versus the control.

EXAMPLES

Materials

PL-Rink amide resin was purchased from Polymer Laboratories. Fmoc-protected amino acids were purchased from Nova Biochem. 1H-Benzotriazolium 1[bis(dimethylamino) methylene]-5-chloro-hexafluorophosphate (1-),3-oxide (HCTU) was purchased from Peptides International. Trifluoroacetic acid (TFA), thioanisole, ethanedithiol, and anisole were purchased from Acros. Diethyl ether, sodium hydroxide and acetonitrile were purchased from Fisher. Dulbecco's Modified Eagle's Medium (DMEM) was purchased from Sigma Aldrich. Light scattering (OD625 nm) was measured on a Hewlett Packard 8453 UV-Visible Spectrophotometer employing a 1 cm pathlength cell.

Peptide Synthesis:

All peptides were prepared on PL-Rink amide resin via automated Fmoc-based peptide synthesis employing an ABI 433A peptide synthesizer and HCTU activation. Resin-bound peptide was cleaved and side chains deprotected using a cleavage cocktail of TFA/thioanisole/ethanedithiol/anisole (90:5:3:2) for 2 hr under an $N_2$ atmosphere. The resin was filtered and the peptide precipitated from the filtrate using cold diethyl ether. Crude peptide was purified by RP-HPLC (preparative Vydac C18 peptide/protein column). For MARG1 and MAX1, purification was performed at 40° C. employing an isocratic gradient at 0% B for 2 minutes then a linear gradient from 0 to 15% B over 10 minutes then, 15 to 100% B over 149 min, where solvent A is 0.1% TFA in water and solvent B is 90% acetonitrile, 10% water, and 0.1% TFA. MARG1 elutes at 35 min and MAX1 elutes at 33 min. The resulting peptide solution was frozen via $N_2$(l) and lyophilized to afford pure peptide as the TFA salt which was used in all assays.

Figure 6:
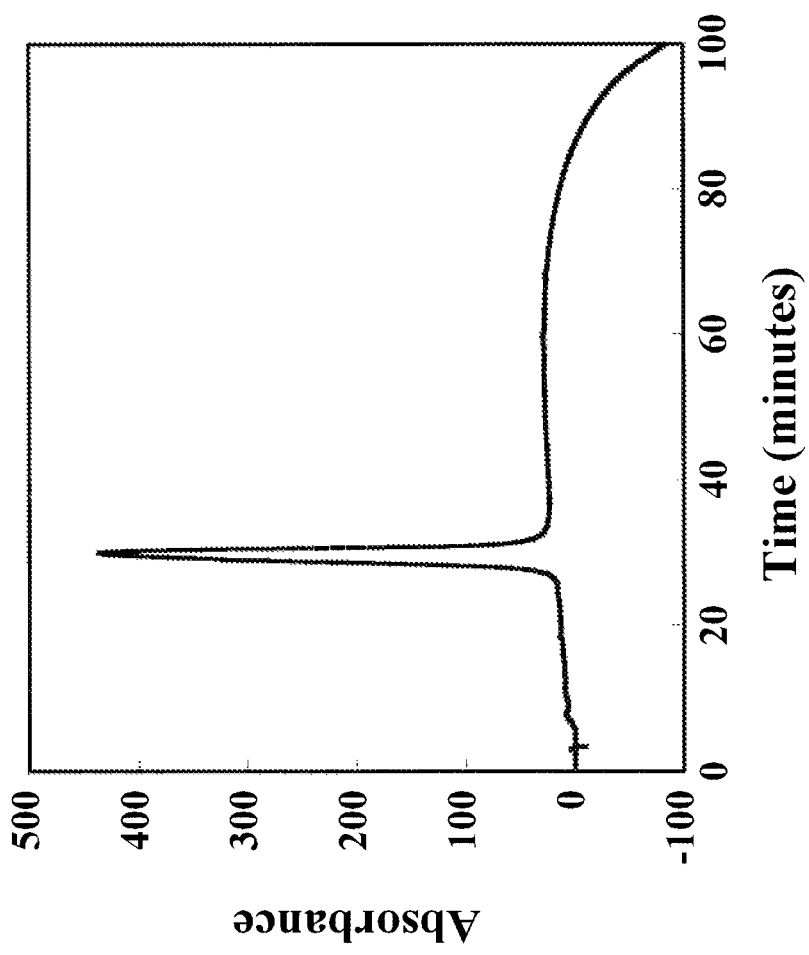
FIG. 6 shows an analytical RP-HPLC chromatogram of Purified MARG1.
Figure 7:
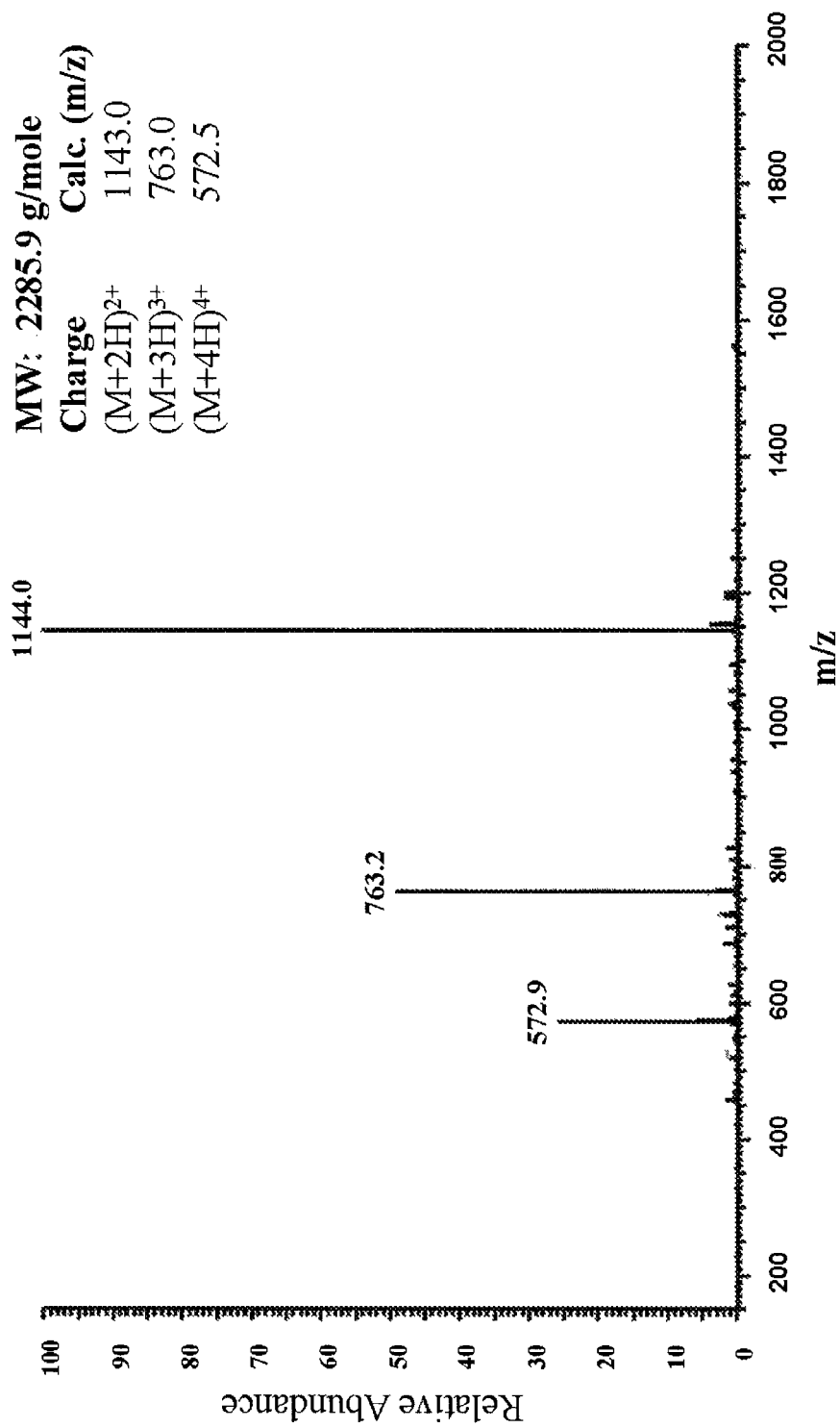
FIG. 7 shows an ESI (+) Mass Spectrum of Purified MARG1.
Figure 8:
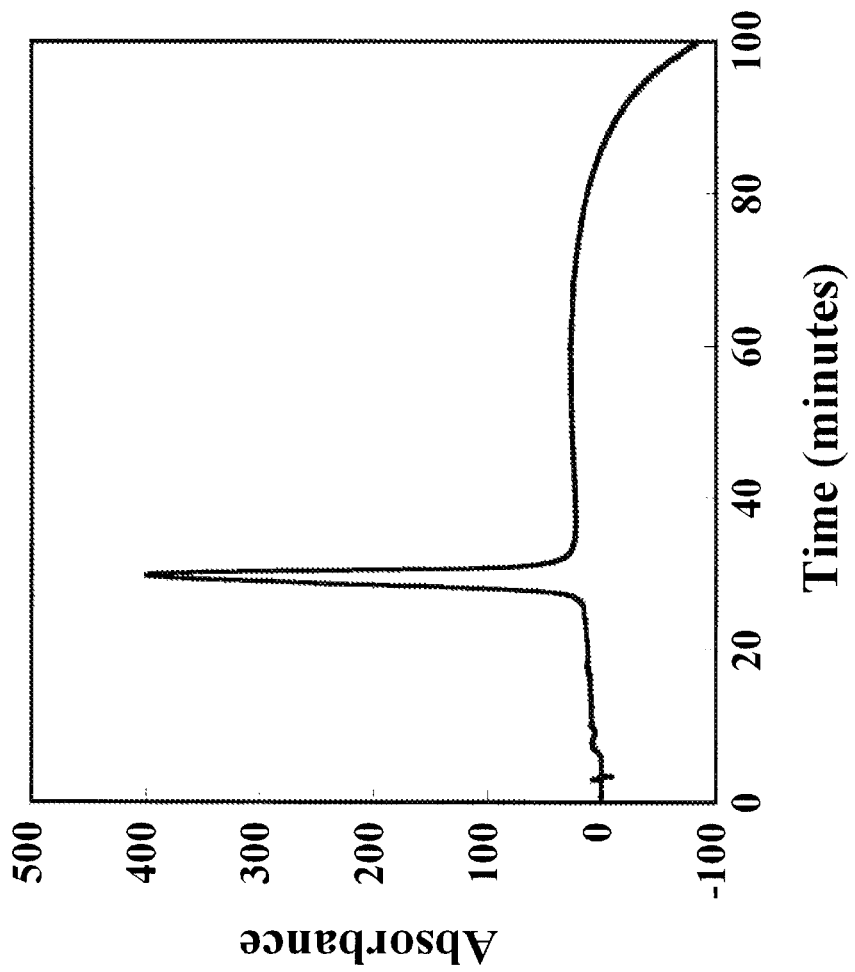
FIG. 8 shows an analytical RP-HPLC chromatogram of Purified MAX1.
Figure 9:
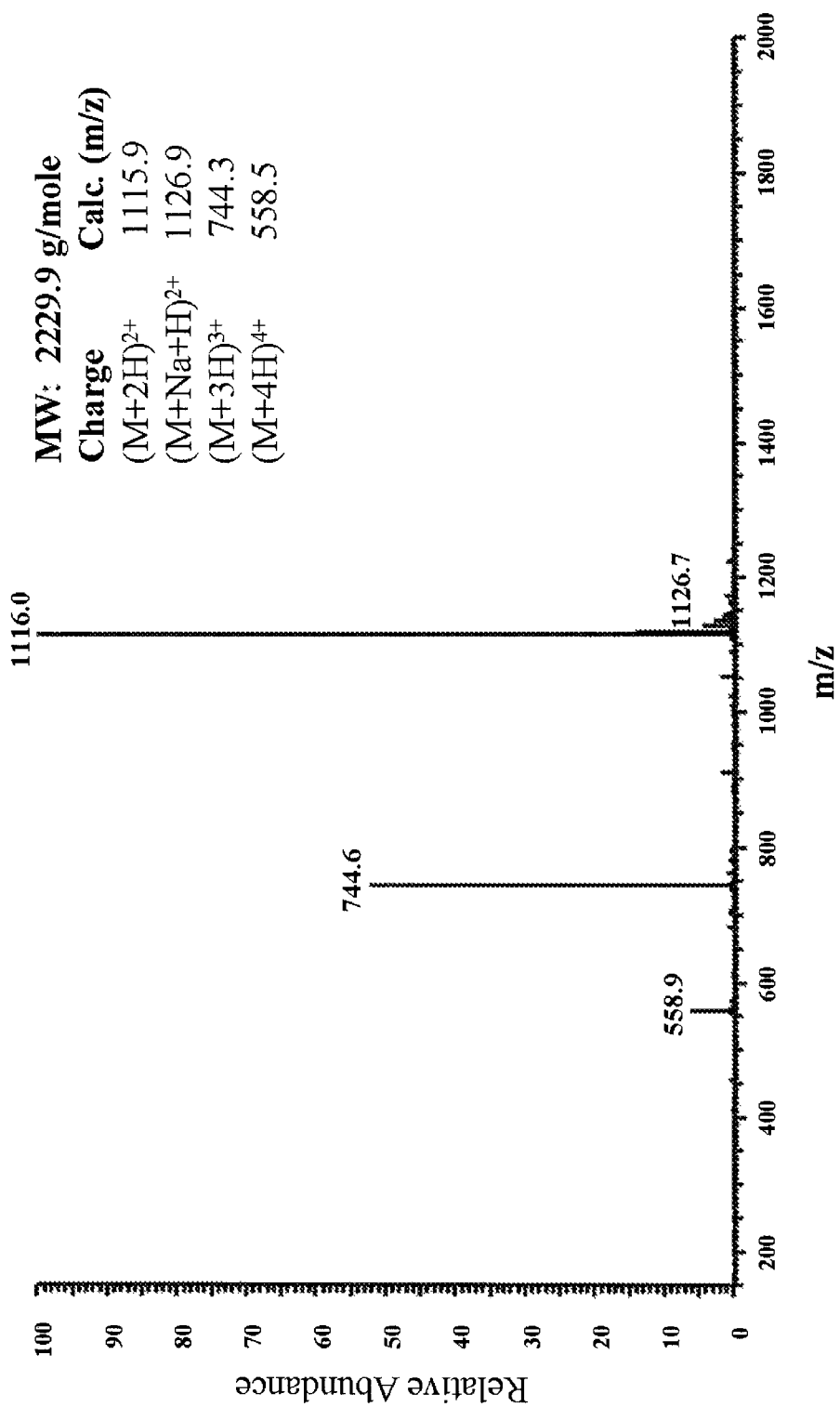
FIG. 9 shows an ESI (+) Mass Spectrum of Purified MAX1.

FIG. 6 shows an analytical RP-HPLC chromatogram of Purified MARG1, and FIG. 7 shows an ESI (+) Mass Spectrum of Purified MARG1. FIG. 8 shows an analytical RP-HPLC chromatogram of Purified MAX1, and FIG. 9 shows an ESI (+) Mass Spectrum of Purified MAX1.

Circular Dichroism Spectroscopy:

CD wavelength spectra were collected on a Jasco J-810 Spectropolarimeter using a 0.1 mm pathlength quartz water-jacketed cell. Briefly, 75 µL of a 1 wt % peptide stock solution in chilled H$_2$O was prepared, followed by the addition of 75 µL chilled DMEM, resulting in a 0.5 wt % peptide solution. This solution (125 µL) was quickly transferred to the water-jacketed cell at 37° C., where gelation was initiated, and ellipticity at 216 nm was monitored over time until equilibrium has been reached (1 hour). A wavelength scan monitoring the ellipticity from 260 nm to 205 nm was performed after 1 hour. For the wavelength spectra of the unfolded peptide, 125 µL of a 1 wt % peptide stock solution in chilled water was directly introduced to the water-jacketed cell and ellipticity was monitored from 260 nm to 205 nm at 10° C. Raw data were converted to mean residue ellipticity using the following equation, $[\theta]=(\theta \text{ obs}/10*1*c)/r$, where θ obs is the measured ellipticity (mdeg), 0.01 is the pathlength of the cell (cm), c is the concentration (M) and r is the number of residues (20).

Figure 10:
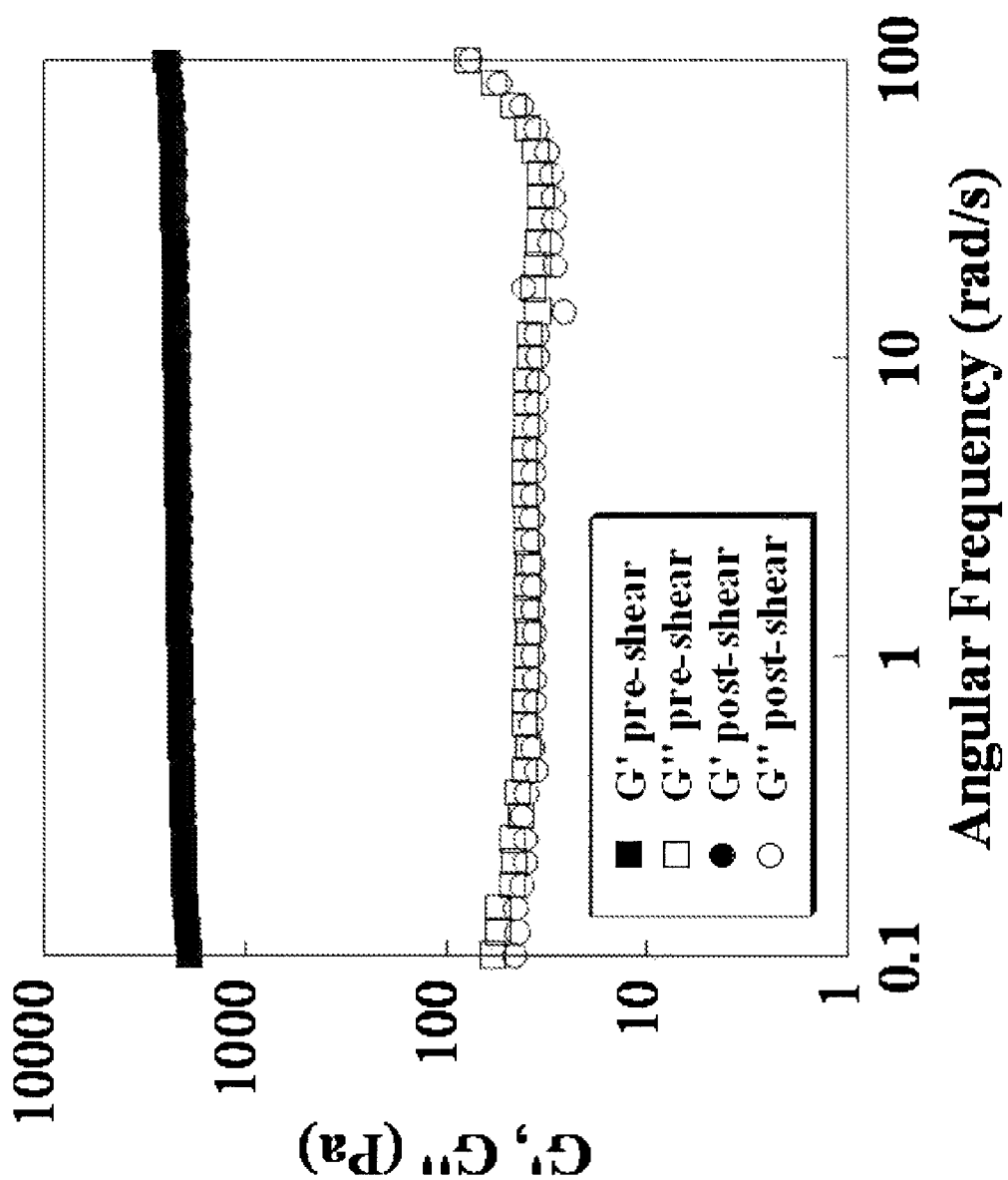
FIG. 10 shows oscillatory shear rheology dynamic frequency sweeps of a 2 wt % MARG1 hydrogel before and after application of 1000% strain.
Figure 11:
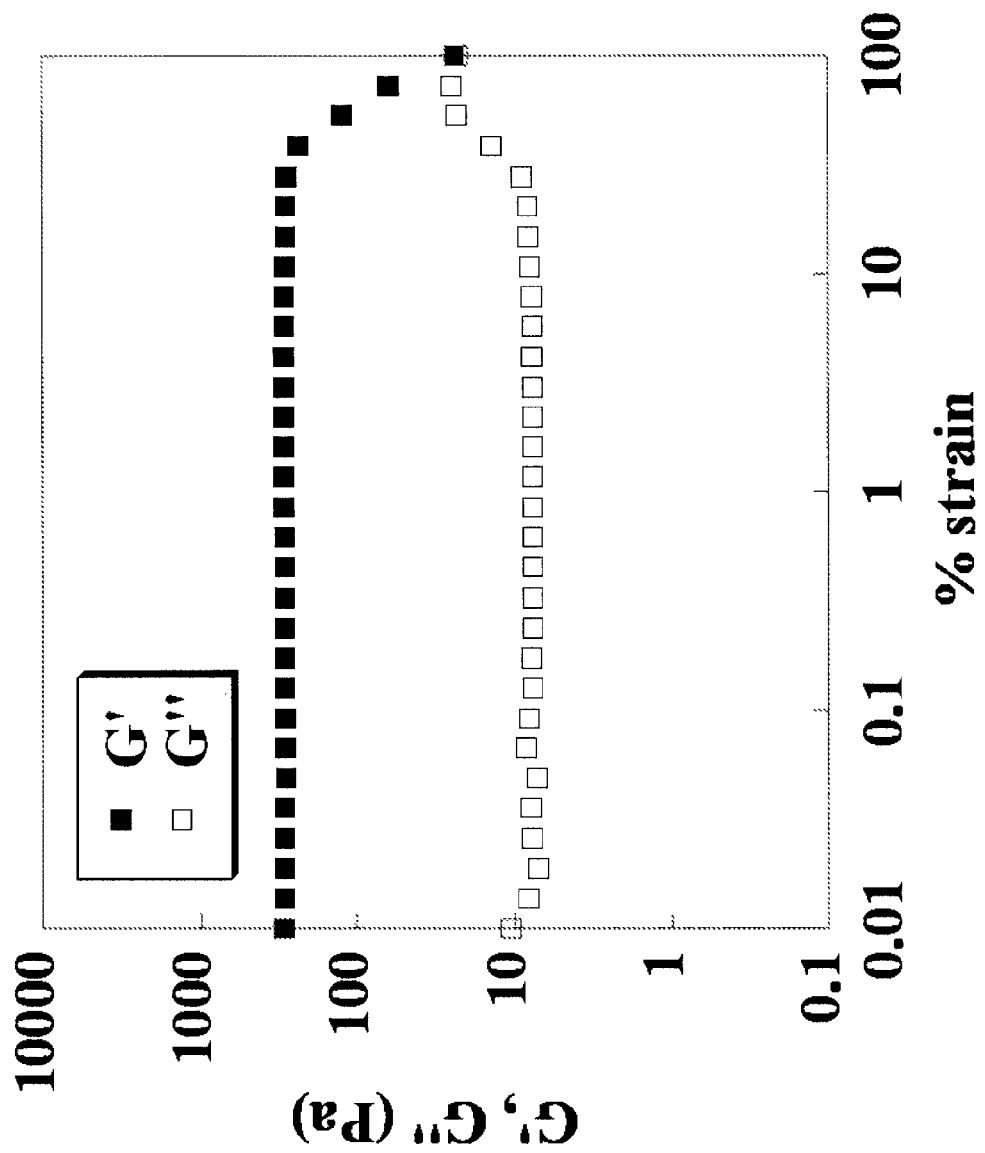
FIG. 11 shows an oscillatory shear rheology dynamic strain sweep of a 1 wt % MARG1 hydrogel showing the storage modulus (G') and loss modulus (G") over a range of applied strains (0.1-100%).

Oscillatory Rheology:

Oscillatory shear rheology experiments were performed on an Anton Paar Physica MCR 500 rheometer using a 25 mm stainless steel parallel plate geometry with a gap height of 0.5 mm. For hydrogel preparation, a chilled 4 wt % MARG1 stock was prepared (10 mg MARG1 in 250 µL H$_2$O), followed by the addition of 250 µL of chilled DMEM cell culture media to initiate folding and self-assembly. Next, 400 µL of the resultant 2 wt % MARG1 solution was quickly transferred to the rheometer plate preequilibrated to 5° C. and the tool was lowered to a gap height of 0.5 mm. The temperature of the plate was then ramped linearly to 37° C. over 100 seconds. A dynamic time sweep was performed at 37° C. (0.2% strain, 6 rad/s) for 1 hr monitoring the storage modulus (G') over time. Next, 1000% strain was applied for 30 seconds to disrupt the hydrogel network (37° C., 6 rad/s), followed by a decrease of strain back to 0.2% where the storage modulus was monitored at 37° C. (6 rad/s) for 1 hr. Dynamic frequency sweep experiments were performed on the 2 wt % MARG1 hydrogel before and after the application of 1000% strain, where G' and G" were monitored over angular frequencies ranging from 0.1 to 100 rads (0.2% strain, 37° C.). In addition, dynamic strain sweep experiments indicated that the yield strain for MARG1 gels is approximately 20%. This indicates that when 1000% strain is applied, as in FIG. 1B, the decrease in the storage modulus is due to shear thinning and not tool slippage. FIG. 10 shows oscillatory shear rheology dynamic frequency sweeps of a 2 wt % MARG1 hydrogel before and after application of 1000% strain. FIG. 11 shows an oscillatory shear rheology dynamic strain sweep of a 1 wt % MARG1 hydrogel showing the storage modulus (G') and loss modulus (G") over a range of applied strains (0.1-100%).

Antibacterial Assays:

Hydrogels for the antibacterial assays were prepared in separate wells of 96-well tissue culture-treated polystyrene plates (Costar 3595). For a given well, 35 µL of a peptide stock solution (4 wt % peptide in sterile filtered H$_2$O) was introduced, followed by the addition of 35 µL of serum-free Dulbeccos Modified Eagles Medium (DMEM; Sigma D6546) to initiate gelation. The resulting 2 wt % hydrogels (70 µL final volume; diameter=8 mm; thickness=2 mm) were allowed to incubate at 37° C. for 2 hours. Then an additional 200 µL of DMEM was added and the gels were equilibrated overnight at 37° C. Prior to the start of the assay this media was removed from the top of all of the hydrogels.

Bacterial stock solutions were prepared from powder bacteria supplied in separate vials which were purchased from American Type Culture Collection® (MRSA, 33591; MSSA, 25923). Bacteria strains from each vial were suspended in 500 µL Tryptic Soy Broth (TSB; Bacto 211824) and quadrant streaked on Trypticase™ Soy Agar plates with 5% sheep's blood (BBL 221239), followed by incubation at 37° C. overnight. After which time, colonies from the fourth quadrant were transferred to a fresh agar plate and quadrant streaked followed by incubation for 24 hours. For each bacterial strain, one colony of bacteria from the fourth quadrant of the second agar plate was suspended in 1 mL of TSB in a 1 mL Ependorf tube. The optical density of this suspension was adjusted to $OD_{625nm}=0.1$ AU by the addition of TSB, resulting in a $10^8$ colony-forming units (CFU)/mL bacterial stock solution.

For each assay, 100 µL of bacteria-free TSB was introduced onto the surface of the hydrogels. Next, 100 µL of the $10^8$ CFU/mL bacterial stock solution was introduced to the surface of a given hydrogel and serial 1:10 dilutions were performed across the plate, resulting in final bacterial concentrations of $2 \times 10^2$, $2 \times 10^3$, $2 \times 10^4$, $2 \times 10^5$, $2 \times 10^6$, $2 \times 10^7$, $2 \times 10^8$ and $2 \times 10^9$ CFU/dm$^2$ respectively, for each of eight wells. Bacteria were incubated for 24 h on MARG1, control MAX1, and TCTP surfaces at 37° C. (initial pH=7.0). After this, bacterial growth was monitored by measuring $OD_{625nm}$ of the liquid above the gel by adding 100 µL of bacteria-free TSB to the surfaces, gently mixing and transferring the supernatant to a cuvette. Corrected $OD_{625nm}$ values were calculated to correct for dilution and to normalize for scattering that occurs for each individual bacterial strain. The following method was used.

For all bacteria assays utilizing UV-Vis spectroscopy to monitor bacterial proliferation, data are reported as a corrected optical density at 625 nm Spectral fluctuations due to scattering, caused by the large particle diameter of bacteria, is normalized for by using multi wavelength measurements at 625 nm and 1100 nm. Therefore, the corrected $OD_{625nm}$ was calculated as follows:

$$\text{Corrected } OD_{625nm} = 2(\text{Observed } OD_{625nm} - \Delta OD_{1100nm}),$$

where the multiplication factor of 2 accounts for dilution and $$\Delta OD_{1100nm} = \text{Observed } OD_{1100nm} - \text{Expected } OD_{1100nm}.$$

$$\text{The Expected } OD_{1100\,nm} = \frac{\text{Observed } OD_{625\,nm}}{\left(\frac{OD_{625\,nm_{Control}}}{OD_{1100\,nm_{Control}}}\right)_{avg}},$$

where $\left(\frac{OD_{625\,nm_{Control}}}{OD_{1100\,nm_{Control}}}\right)_{avg}$ is constant and is dependent on bacterial species. (Methicillin-resistant *Staphylococcus aureus*=3.20±0.07, Methicillin-susceptible *Staphylococcus aureus*=3.19±0.14)

Each assay reported in FIG. 2 represents triplicate experiments for each bacterial strain. For each strain, at least two additional experiments were performed (each in triplicate) that showed reproducible results consistent with those shown.

Shear-Thin Delivery of MARG1 onto Bacteria-Contaminated Agar:

Hydrogels used for syringe delivery were prepared in a 1 mL sterile syringe (BD, 309602) using a 26G$^{3/8}$ sterile intradermal bevel needle (BD, 305110). A 4 wt % MARG1 stock solution (10 mg MARG1 in 250 µL H$_2$O) was prepared in a 2 mL glass vial, followed by the addition of 250 µL DMEM, resulting in a 2 wt % MARG1 solution. This solution was quickly drawn into a 1 mL syringe through a 26G$^{3/8}$ needle and allowed to incubate at 37° C. for 1 hour prior to performing experiments.

Mueller Hinton (MH) agar surfaces were prepared in 2-well sterile borosilicate confocal plates (Lab Tek II, 155379). Briefly, 3.8 g of Mueller Hinton agar (Remel, R454081) was suspended in 100 mL of $H_2O$ and boiled on a hot, stir plate until fully dissolved. Next, the suspension was autoclaved at 121° C. for 15 minutes. Approximately 1.5 mL of this solution was introduced to a well of a 2-well plate and allowed to gel at room temperature for 30 minutes. A $10^8$ CFU/mL MRSA stock solution in TSB was prepared as previously described. For the addition of the bacteria onto the MH agar plates, a sterile cotton swab was submerged into the stock solution of bacteria and then wiped onto the agar. To assure full coverage, the swab was wiped in three directions. After the introduction of bacteria, plates were allowed to incubate at 37° C. for 15 minutes. Next, 2 wt % MARG1 hydrogels were shear-thin delivered to the plates and then allowed to incubate at 37° C. for 24 hr.

Following 24 h of incubation at 37° C., 200 µL of LIVE/DEAD BacLight (Molecular Probes L13152) commercial solution (prepared according to the insert directions) was added to each well resulting in a final concentration of 6 µM SYTO9 and 30 µM propidium iodide. Cells were immediately imaged using 20× magnification on a Zeiss 510 Laser Scanning Confocal Microscope. When excited at 488 nm with an Ar/Kr laser, bacteria with intact membranes displayed green fluorescence (Em=500 mm) and bacteria with compromised membranes fluoresced red (Em=635 nm).

Assessment of Cytotoxicity of MARG1 Hydrogel Towards Mammalian Cells:

C3H10t1/2 mesenchymal stem cells (ATCC # CCL-226) were cultured using Dulbecco's Modified Eagle's Medium (DMEM, Sigma Aldrich, D6546) supplemented with 10% Fetal Bovine Serum, 5 mM L-Glutamine, 50 µg/mL Gentamicin at 37° C. in 5% $CO_2$. Cells were cultured in T75 cell culture flasks. Cells were kept in culture for seven passages and used for cellular viability on passage number 7. For cell plating, cells were trypsinized and counted using a hemacytometer. The resultant cell suspension was introduced to the hydrogel and control surfaces such that a cell loading density of 30,000 cells/$cm^2$ was achieved. These samples were incubated for 24 hours at 37° C., 5% $CO_2$. For cellular viability assays, the media above the hydrogel and borosilicate control surfaces was removed and a solution of 1 µM calcein AM and 2 µM ethidium homodimer in DMEM supplemented with 25 mM HEPES (prepared as described above in the live/dead assay) was introduced. Samples were imaged using a Zeiss 510 laser scanning confocal microscope at a magnification of 10×.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A peptide comprising the sequence VKVKVRVKV$^D$-PPTKVKVRVKV-$NH_2$.

2. A method of killing bacteria, comprising a step of contacting the bacteria with a hydrogel comprising the peptide of claim 1.

3. The method of claim 2, wherein the bacteria comprise *Staphylococcus aureus*.

4. The method of claim 2, wherein the bacteria comprise Methicillin-Resistant *Staphylococcus aureus*.

5. The method of claim 2, wherein the contacting comprises delivering the hydrogel with a syringe to the bacteria.

6. The method of claim 2, wherein the hydrogel is subjected to sufficient shear stress to convert the hydrogel to a lower viscosity, flowable fluid; the lower viscosity, flowable fluid is delivered to a target site containing the bacteria; and the shear stress is relieved, thereby converting the lower viscosity, flowable fluid back to a hydrogel.

7. A method of inhibiting proliferation of bacteria, comprising applying to the bacteria an effective amount a hydrogel comprising the peptide of claim 1.

* * * * *